United States Patent
Tur et al.

(10) Patent No.: US 9,332,966 B2
(45) Date of Patent: May 10, 2016

(54) METHODS AND SYSTEMS FOR DATA COMMUNICATION IN AN ULTRASOUND SYSTEM

(71) Applicant: General Electric Company, Schenectady, NY (US)

(72) Inventors: Ronen Tur, Tirat Carmel (IL); Alexander Sokulin, Tirat Carmel (IL)

(73) Assignee: General Electric Company, Schenectady, NY (US)

(*) Notice: Subject to any disclaimer, the term of this patent is extended or adjusted under 35 U.S.C. 154(b) by 148 days.

(21) Appl. No.: 14/172,267

(22) Filed: Feb. 4, 2014

(65) Prior Publication Data

US 2015/0216511 A1 Aug. 6, 2015

(51) Int. Cl.
*A61B 8/14* (2006.01)
*A61B 8/00* (2006.01)

(52) U.S. Cl.
CPC . *A61B 8/565* (2013.01); *A61B 8/14* (2013.01); *A61B 8/4405* (2013.01); *A61B 8/4427* (2013.01); *A61B 8/465* (2013.01)

(58) Field of Classification Search
CPC .................................. A61B 8/14; A61B 8/565
See application file for complete search history.

(56) References Cited

U.S. PATENT DOCUMENTS

| | | | |
|---|---|---|---|
| 6,023,977 A * | 2/2000 | Langdon | G01N 29/06 367/87 |
| 7,436,912 B2 | 10/2008 | Fudge et al. | |
| 7,804,736 B2 | 9/2010 | Alexandru | |
| 8,490,489 B2 | 7/2013 | Randall et al. | |
| 8,499,635 B2 | 8/2013 | Klessel et al. | |
| 2005/0049496 A1* | 3/2005 | Guracar | G01S 15/8981 600/437 |
| 2007/0232906 A1 | 10/2007 | Alexandru | |
| 2011/0196237 A1 | 8/2011 | Pelissier et al. | |
| 2011/0301464 A1 | 12/2011 | Yoo et al. | |

* cited by examiner

*Primary Examiner* — Mark Remaly
(74) *Attorney, Agent, or Firm* — Dean D. Small; The Small Patent Law Group, LLC (57) ABSTRACT

Methods and systems for data communication in an ultrasound system are provided. One method includes acquiring ultrasound data using an ultrasound probe having a plurality of transducer elements, wherein the ultrasound data includes echo information acquired from the plurality of transducer elements and the ultrasound data is acquired using a plurality of transmit events of the ultrasound probe. The method also includes digitizing the acquired ultrasound data. The method further includes communicating a subset of the digitized ultrasound data for at least some of the plurality of transmit events, wherein the subsets of communicated digitized ultrasound data are different for the plurality transmit events.

16 Claims, 6 Drawing Sheets

FIG. 8

METHODS AND SYSTEMS FOR DATA COMMUNICATION IN AN ULTRASOUND SYSTEM

BACKGROUND OF THE INVENTION

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound systems are controllable to operate in different modes of operation to perform the different scans. The signals received at the probe are then communicated and processed at a back end.

The transducers in medical ultrasound probes typically contain array(s) having a large number of transducer elements, which may include associated per-element electronic circuits. Additionally, the front end generally includes a number of data channels. Conventional medical ultrasound probes are designed to support signals with a certain bandwidth as acquired and communicated in the data channels. The sampling method(s), digital interfaces, and processing blocks in the processing chain are designed accordingly, and usually limit the maximal bandwidth. Thus, these systems may have limited bandwidth and only allow processing signals with bandwidths that are smaller than desirable. Moreover, as bandwidth requirements increase, in conventional systems, in order to meet these bandwidth increase requirements, the complexity and size of the data interfaces increase, which can also result in an increase in power requirements.

For example, in conventional systems, increasing system bandwidth is provided by increasing the analog to digital converter (ADC) sampling rate and digital interface transfer rate. However, increasing the sampling rate of the ADC (and also changing the output interface to a higher throughput interface) increases the cost and complexity of the system.

BRIEF DESCRIPTION OF THE INVENTION

In accordance with one embodiment, a method for communicating data in an ultrasound system is provided. The method includes acquiring ultrasound data using an ultrasound probe having a plurality of transducer elements, wherein the ultrasound data includes echo information acquired from the plurality of transducer elements and the ultrasound data is acquired using a plurality of transmit events of the ultrasound probe. The method also includes digitizing the acquired ultrasound data and communicating a subset of the digitized ultrasound data for at least some of the plurality of transmit events, wherein the subsets of communicated digitized ultrasound data are different for the plurality transmit events.

In accordance with another embodiment, an ultrasound system is provided that includes an ultrasound probe having a transducer array for acquiring ultrasound data including echo information during an imaging mode of operation, wherein the ultrasound probe is configured to acquire the ultrasound data using a plurality of transmit events. The ultrasound system further includes a digitizer configured to digitize the acquired ultrasound data. The ultrasound system also includes a transmit event controller configured to communicate a subset of the digitized ultrasound data for at least some of the plurality of transmit events, wherein the subsets of communicated digitized ultrasound data are different for the plurality transmit events.

DETAILED DESCRIPTION OF THE INVENTION

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide bandwidth enhancement in ultrasound systems enabling the system to support higher effective bandwidths. For example, various embodiments allow processing signals with a higher bandwidth than the system can handle using some conventional processing methods. The increased bandwidth signals enable better image quality due to better resolution. Lowering the complexity of interfaces with various embodiments also reduces technical risks of high data rate interfaces and may reduce cost. Additionally, lowering power with various embodiments can enable miniaturization and increase the scans per battery life (such as in portable systems). Additionally, existing system bandwidth may be enhanced without redesign of hardware. Various embodiments, thus, may reduce the complexity of data interfaces and/or reduce the power of data interfaces used to increase the processing bandwidth of the system.

Various embodiments also overcome the Nyquist limitation of ultrasound systems. One technical effect of some embodiments is increased system signal bandwidth.

It should be noted that various embodiments described herein that generate or form images may include processing for forming images that in some embodiments includes beamforming and in other embodiments does not include beamforming. Also, forming of images may be performed using channel combinations that may originate from more than one transmit event (e.g., synthetic aperture techniques) as described in more detail herein.

Figure 1:
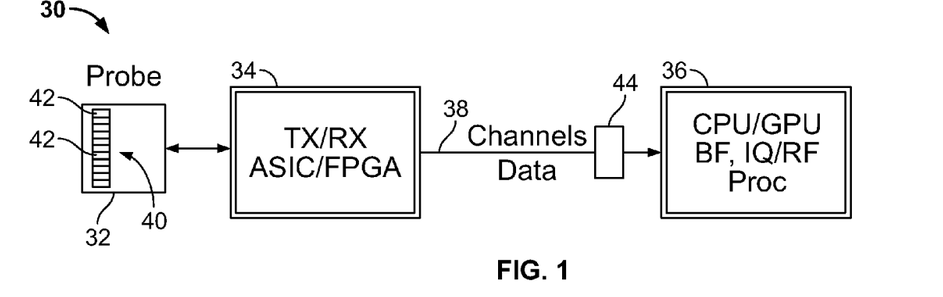
FIG. 1 is a simplified block diagram of an ultrasound system formed in accordance with various embodiments.

In various embodiments, ultrasound processing to form images is performed, for example, including ultrasound beamforming or other types of ultrasound image reconstruction, in software, hardware, or a combination thereof. One implementation of an ultrasound system, such as shown in FIG. 1, combines data from multiple transmit events and can increase the effective bandwidth of the system. FIG. 1 illustrates a simplified block diagram of an ultrasound system 30. The ultrasound system 30 is configured to acquire ultrasound data using a probe 32 having a transducer array 40 (with a plurality of transducer elements 42), wherein transmission and reception functionality, such as transmission and reception of ultrasound signals are provided by a front end 34. In another embodiment, the probe 32 may contain electronics, for example, for performing partial beamforming of groups of adjacent elements (such as using a SAP—Sub Array Processor) and/or transmitter electronics. The front end 34 in various embodiments includes a beamformer as described in more detail in connection with FIG. 2. For example, a hardware implemented beamformer may be provided to perform beamforming of transmit signals or beamforming of groups of received channels data 38 as described herein.

The front end 34 also generally includes a transmitter/receiver, which may be implemented in, for example, an application specific integrated circuit (ASIC) or a field-programmable gate array (FPGA). An ADC 44 is also provided and connected to the receiver portion of the front end 34.

It should be noted that the transducer elements 42 may have a one-dimensional, two-dimensional, or three-dimensional arrangement. Additionally, different types of transducer arrays 40 may be provided, such as a linear array or an arcuate array.

The front end 34 is connected to a back end 36, for example, via one or more communication lines 38, which may include one or more buses, such as a Peripheral Component Interconnect Express (PCIe) bus or other bus (e.g., a high bandwidth bus typically having several GB/sec. transfer rate). Alternately, the communication channel may be a wireless link. The communication line(s) 38 communicates ultrasound data from the front end 34 to the back end 36, and may include one or more data channels (e.g., for communicating beamformed data). The data that is communicated from the front end 34 to the back end 34 is generally a digitized (communicated through the ADC 44) and optionally a transformed version of the channel data as acquired by the probe 32. The transformation may include, for example, filtering/decimation, complex demodulation, or other standard signal processing operations.

The back end 36 generally includes processing units, which may include an additional beamformer, or other type of image reconstruction unit, and an IQ/RF processor as described in more detail herein. The processing functions may be performed by one or more general purpose processors, such as CPUs, GPUs, and/or DSPs, among others.

In some embodiments, the ultrasound system 30 operates to perform real-time three-dimensional (3D) or four-dimensional (4D) scanning that transmits and/or acquires multiple beams simultaneously or concurrently. The ultrasound system 30 in various embodiments includes a processor (e.g., CPU and/or GPU) that receives data from the plurality of channels 38 corresponding to the transducer elements 42. Thus, data transfer from all or a subset of the channels 38 is provided in some embodiments for generating images.

It should be noted that software beamforming may be used and includes performing any type of beamforming technique, which may include performing beamforming techniques in software that can be performed in hardware. It also should be noted that when reference is made herein to beamforming techniques, this generally refers to any type of image forming that may be performed by the ultrasound system.

In operation a transmitter of the front end 34, under the guidance of a beamformer (transmit beamformer), drives the array of transducer elements 42 (e.g., piezoelectric elements) within the probe 32 to emit pulsed ultrasonic signals into a body. A variety of geometries may be used. The ultrasonic signals are back-scattered from structures in the body, like blood cells or muscular tissue, to produce echoes that return to the elements 42. The echoes are received by a receiver of the front end 34 and then communicated to the ADC 44 to perform digitization of the signals (analog to digital conversion) and optionally a demodulator (not shown), which may be different components or implemented in a single component, for example, in an ASIC. The demodulator may be, for example, a complex demodulator that performs digital demodulation, and optionally filtering and decimation.

Figure 2:
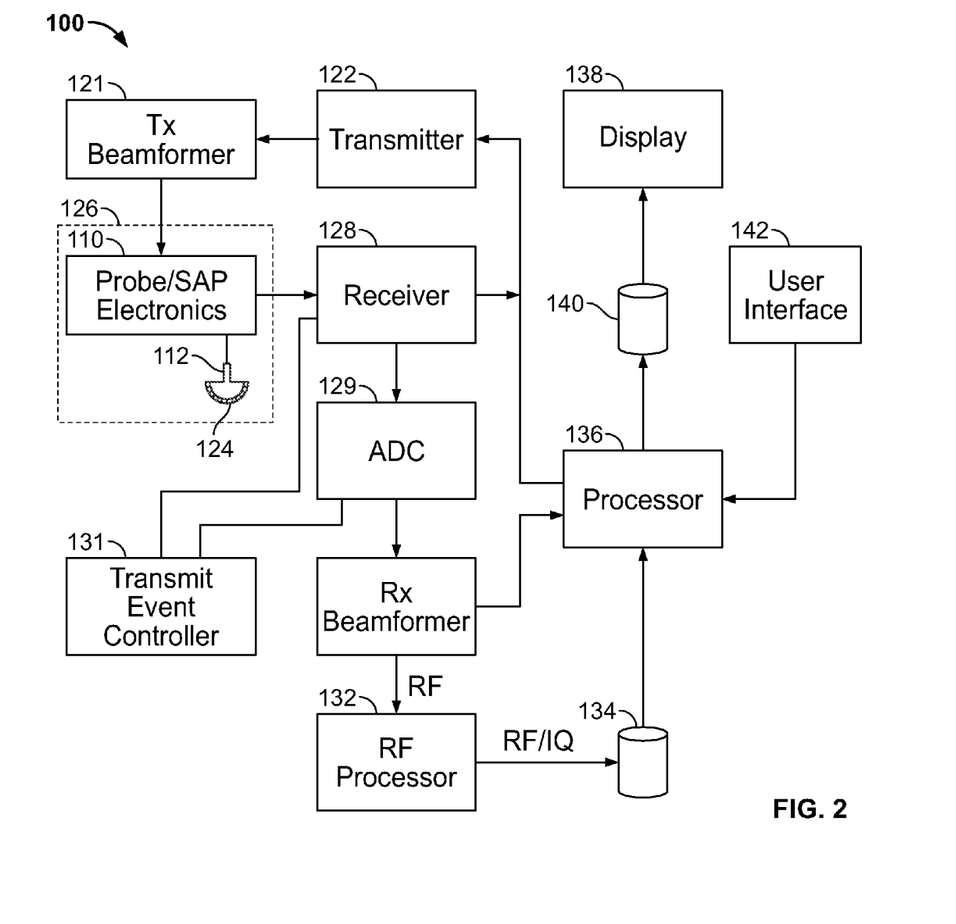
FIG. 2 is a detailed block diagram of an ultrasound system formed in accordance with various embodiments.

FIG. 2 is a more detailed block diagram of an ultrasound system 100 that may be embodied, for example, as the ultrasound imaging system 30 shown in FIG. 1. In the illustrated embodiment, the ultrasound system 100 includes a probe 126 (which may be embodied as the probe 32 shown in FIG. 1) having a transmitter 122 and probe/SAP electronics 110. The transmitter 122 transmits a signal to a transmit beamformer 121 which in turn drives the transducer elements 124 within the transducer array 112. The transducer elements 124 emit pulsed ultrasonic signals into the patient. A variety of a geometries and configurations may be used for the array 112. Further, the array 112 of transducer elements 124 may be provided as part of, for example, different types of ultrasound probes.

The transducer elements 124, for example piezoelectric crystals, emit pulsed ultrasonic signals into a body (e.g., patient) or volume. At least a portion of the pulsed ultrasonic signals back-scatter from a region of interest (ROI) (e.g., breast tissues, liver tissues, cardiac tissues, prostate tissues, and the like) to produce echoes. The echoes are delayed in time according to a depth, and are received by the transducer elements 124 within the transducer array 112. The ultrasonic signals may be used for imaging, among other uses.

The transducer array 112 may have a variety of array geometries and configurations for the transducer elements 124, which may be provided as part of, for example, different types of ultrasound probes. The probe/SAP electronics 110 may be used to control the switching of the transducer elements 124. The probe/SAP electronics 110 may also be used to group the transducer elements 124 into one or more sub-apertures.

The transducer elements 124 convert the received echo signals into electrical signals, which may be received by a receiver 128. The electrical signals representing the received echoes are digitized by an ADC 129 (which may be embodied as the ADC 44 shown in FIG. 1). A transmit event controller 131 is provided that controls the combining of data resulting from multiple transmit events. For example, the transmit event controller 131 determines or selects the data to be communicated from the receiver 128 or digitized by the ADC 129, which may include combining data from multiple transmit events (e.g., communicating half the data from one transmit event and then the other half of the data in a second transmit event). It should be noted that in various embodiment a transmit event includes firing of the transducer elements 124 to define a single transmit event. The firings may be lines (which in some embodiments have a width, and generally referred to as wide lines) or plane waves in various embodiments.

The digitized signals are then passed through a receive beamformer 130, which performs beamforming on the received echoes and outputs an RF signal. The RF signal is then provided to an RF processor 132 that processes the RF signal. Alternatively, the RF processor 132 may include a complex demodulator (not shown) that demodulates the RF signal to form IQ data pairs representative of the echo signals. The RF or IQ signal data may then be provided directly to a memory 134 for storage (e.g., temporary storage). Optionally, the output of the beamformer 130 may be passed directly to a processor 136, which may be a diagnostic circuit or image processing circuit.

The processor 136 processes the acquired ultrasound information (e.g., RF signal data or IQ data pairs) and prepare frames of ultrasound information for display on the display 138. The processor 136 may include one or more separate processing components. For example, the processor 136 may include a central processing unit (CPU), a microprocessor, a graphics processing unit (GPU), or any other electronic component capable of processing inputted data according to specific logical instructions. Having the processor 136 that includes a GPU may be advantageous for computation-intensive operations, such as volume-rendering.

The processor 136 is adapted to perform one or more processing operations according to a plurality of selectable ultrasound modalities on the acquired ultrasound information. Acquired ultrasound information may be processed in real-time during a scanning or therapy session as the echo signals are received. Additionally or alternatively, the ultrasound information may be stored temporarily in the memory 134 during a scanning session and processed in less than real-time in a live or off-line operation. An image memory 140 is included for storing processed frames of acquired ultrasound information that are not scheduled to be displayed immediately or to store post-processed images (e.g., shear-wave images, strain images). The image memory 140 may comprise any known data storage medium, for example, a permanent storage medium, removable storage medium, etc.

The processor 136 is connected to a user interface 142 that controls operation of the processor 136 and the display 138 as explained below in more detail and is configured to receive inputs from the user, for example a keyboard, a keypad, buttons, a touchscreen. The display 138 may include one or more monitors that present patient information, including diagnostic and therapeutic ultrasound images to the user for review, diagnosis, analysis, and treatment. The display 138 may automatically display, for example, one or more 2D, 3D, or 4D ultrasound data sets stored in the memory 134 or 140 or currently being acquired. One or both of the memory 134 and the memory 140 may store 3D data sets of the ultrasound data, where such 3D data sets are accessed to present 2D and 3D images. For example, a 3D ultrasound data set may be mapped into the corresponding memory 134 or 140, as well as one or more reference planes. The processing of the data, including the data sets, may be based in part on user inputs, for example, user selections received at the user interface 142.

In operation, the system 100 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data may be acquired by moving the probe 126, such as along a linear or curvilinear path, while scanning the ROI. At each linear or arcuate position, the probe 126 obtains scan planes that are stored in the memory 134.

Figure 3:
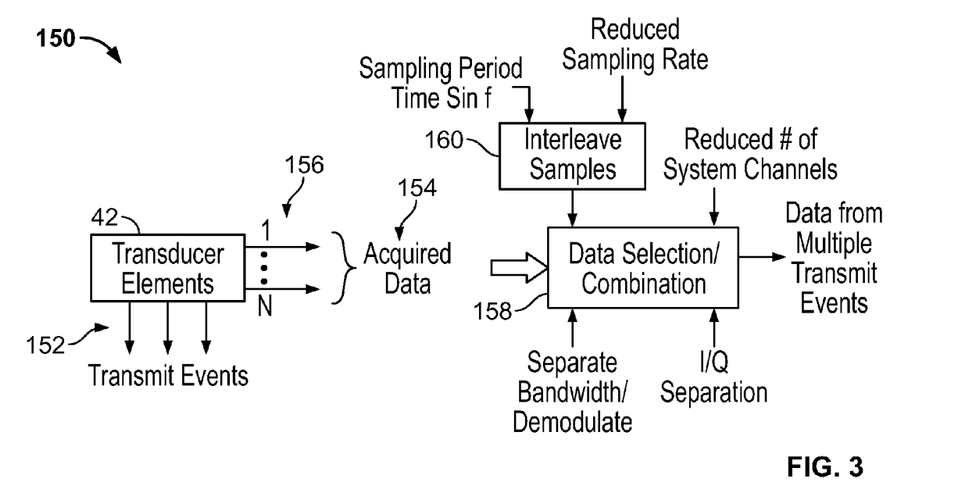
FIG. 3 is a block diagram illustrating an ultrasound data acquisition and communication work flow performed in accordance with various embodiments.

FIG. 3 illustrates an ultrasound data acquisition and transfer work flow 150 performed in accordance with various embodiments. The work flow 150 in some embodiments provides bandwidth enhancement of an ultrasound system. The work flow 150 controls the data acquired and communicated from a multiple transmit events 152 of the transducer elements 42. In particular, acquired ultrasound data 154 is received via a plurality of receive channels 156. A determination is then made as to the acquired ultrasound data 154 to be communicated. For example, a data selection/combination is performed at 158 (such as by the transmit event controller 131 shown in FIG. 2), which includes for example, determining the data to be communicated or combined from the plurality of receive channels 156. In various embodiments, a subset of the acquired data 154 from the plurality of receive channels 156 (e.g., half of the data, such as data from half of the plurality of receive channels 156 or different samples) is communicated resulting in different data that is used from each of the transmit events 152, which may be combined in different manners as described herein. Thus, for example, a complete set of acquired data may be communicated using the subsets of the acquired data 154 from different transmit events 152. In various embodiments, data from less than all of the plurality of receive channels 156 is communicated for multiple different transmit events 152. In some embodiments, more than one transmit is used, such that other factors or multiples may be used.

For example, the data selection/combination at 158 combines data (namely the acquired data 154, such as received echo signals) from multiple transmit events and increases the effective bandwidth of the system. In some embodiments, interleaved data samples 160 are used. For example, in one embodiment, data from two transmit events is combined by interleaving samples from the first and second transmit events, where the data of the second event is acquired with a half a sampling period time shift relative to the first event (thereby increasing the effective bandwidth of the digitized signal by factor of 2). For example, for a 100 mega-samples (Msamples)/sec ADC, a 10 nanosecond gap may be provided between two samples (different subsets). Thus, a 10 nanosecond (nsec) gap may be provided between two consecutive samples of one subset, and a shift of 5 nsec is provided between the two subsets, resulting in effectively 200 Msamples/sec. As another example, for a 50 Msamples/sec ADC, a 20 nsec gap may be provided between two samples. However, it should be appreciated that other sampling period time shifts may be used and the various embodiments are not limited to a half a sampling period time shift (e.g., more or less than half a sampling period time shift).

In another embodiment, if the system bandwidth is limited by the digital interface transferring data from the ADC 129 (shown in FIG. 2), instead of increasing the data rate of the output of the ADC, the effective bandwidth is increased by interleaving samples from two consecutive transmit events, where data of each event is transferred at half the ADC sampling rate.

In another embodiment, the effective bandwidth is increased by combining data from half of the system channels (illustrated as the plurality of receive channels 156) transferred in the first transmit event with another half of the channels transferred in the second transmit. In another embodiment, the effective bandwidth is increased by separating the full bandwidth into two halves, where on each transmit event only half of the data bandwidth is transferred. For example, in one embodiment, demodulating is performed for the lower half band on the first transmit event, and for the upper half band on the second event. In another embodiment, the effective bandwidth is increased by demodulating and transferring the in-phase component (I) on the first transmit event, and quadrature component (Q) on the second event.

It should be noted that in various embodiments, anti-aliasing filtering before ADC is set wide enough for the entire resulting signal bandwidth.

Thus, portions or subsets of the acquired data 154 are used or communicated for multiple transmit events 152, for example, sending half the data in one transmit event and the other half in the second event. For example, in a system having 128 channels, acquired data from channels 1-64 may be sent for a first transmit event and acquired data from channel 65-128 sent for a second transmit event. However, variations and modifications are contemplated. For example, acquired data from even channels may be communicated for the first transmit event and acquired data from odd channels may be communicated for the second transmit event.

It should be noted that when reference is made herein to sending or communicating data from a transmit event, this generally refers to communicating the acquired data for the transmit event (e.g., acquired data resulting from ultrasound firings) for digitization or processing. In various embodiments, the firings for the different transmit events are the same (e.g., two of the same measurements). Accordingly, in various embodiments, for example, all of the transducer elements 42 are sampled, but acquired data from less than all of the transducer elements 42 or receive channels (e.g., half of the receive channels) is communicated from the front end 34 (shown in FIG. 1).

It should be noted that the number of transmit events used can be more than two. For example, the acquired data 154 from more than two transmit events 152 may be used.

It also should be noted that the transmit events do not have to be consecutive or sequential. For example, different spacing or staggering of transmit events from which data is used may be provided.

It further should be noted that even when the object is dynamic, motion correction as known in the art may be applied. Additionally, while the various embodiments are described in connection with an ultrasound system, the various embodiments may be implemented in other medical devices, or imaging devices.

Figure 4:
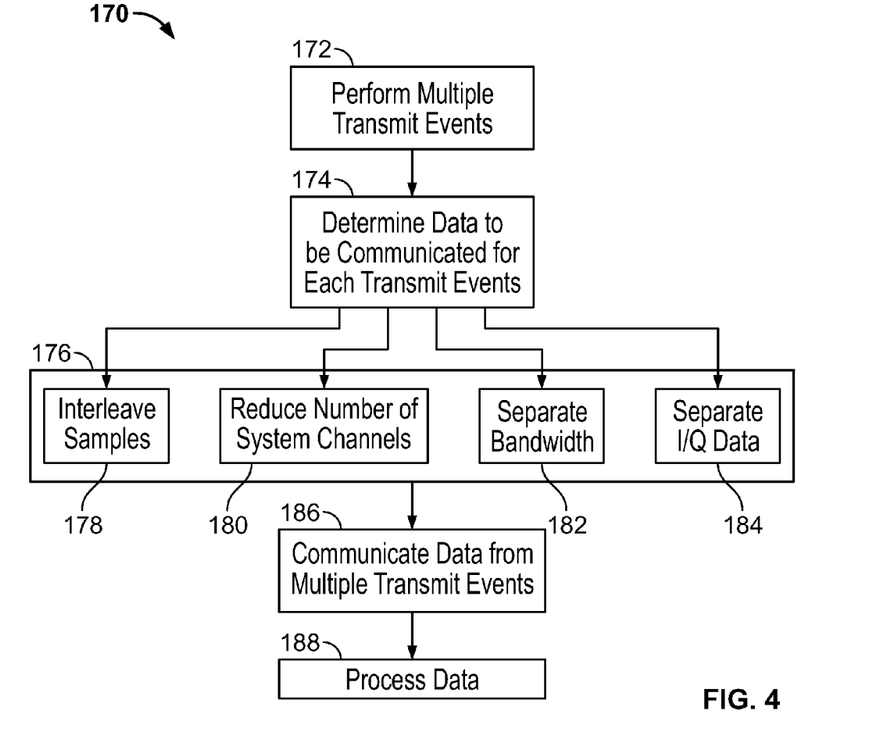
FIG. 4 is a flowchart of a method in accordance with various embodiments.

Various embodiments provide a method 170 for communicating acquired ultrasound data as shown in FIG. 4. The method 170 in various embodiments uses subset or portions of acquired data from multiple transmits events to increase the effective bandwidth of the ultrasound system. The method 170, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the methods may be able to be used as one or more algorithms to direct hardware to perform operations described herein.

In particular, the method 170 includes performing multiple transmit events at 172. In various embodiments, transmit beamforming may be performed to generate ultrasound lines or plane waves (ultrasound firings) from a plurality of transducer elements that are emitted into an object of interest (e.g., a patient). The transmit events are generated using the same transmit beamforming or ultrasound firings for each of the plurality of transmit events. Thus, each of the plurality of transmit events (which may be two or more) from which data is acquired and communicated for processing is the same (e.g., identical firings from the transducer elements).

The method 170 also includes determining at 174 the acquired data to be communicated for each of the transmit events. For example, a determination is made as to which portion or subset of the acquired data to communicate for processing or digitization. In some embodiments, for example, a determination is made at to the channels of acquired data to communicate or use for each of the plurality transmit events. It should be noted that while different subsets of data may be used or communicated for each of the transmit events, in some of the embodiments, overlap may be provided (e.g., data from some of the same channels is communicated for different transmit events). The determination of the data to be communicated for each of the plurality of transmit events may be based on, for example, the desired effective bandwidth or particular application or image scan to be performed. The determination may be predefined or dynamically changed as desired or needed.

The method 170 includes selecting a data transmit event communication scheme at 176 based on the determination at 174. For example, the data from transmit events may be combined differently using one or more of the data transmit event communication schemes. It should be noted that in various embodiments, the data transmit event communication scheme may be any scheme that transmits or uses less than the entire set of data (e.g., data from less than all of the receive channels) acquired by the transducer elements for different ones of a plurality of transmit events. As some examples, the data transmit event communication schemes include interleaving the samples at 178, reducing the number of system channels used at 180, separating the bandwidth at 182, and/or separating the I/Q data at 184, each of which may be performed as described in more detail herein. It should be noted that different data transmit event communication schemes may be used during the same imaging scan. Additionally, a combination of the data transmit event communication schemes may be used for a particular transmission. Also, the data transmit event communication scheme may be manually or automatically selected (e.g., based on system bandwidth requirements) in various embodiments.

The method 170 includes communicating the data from the multiple transmit events at 186. For example, the data from multiple transmit events is communicated from a front end to a back end of the ultrasound system using one or more of the data transmit event communication schemes. The communicated data in various embodiments includes a combination of data (e.g., data from subsets of receive channels) from a plurality of transmit events, which may be sequential or non-sequential transmit events. By combining the data as described herein, increased effective bandwidth may be provided. For example, for a 12.5 MHz bandwidth system, various embodiments allow for an effective bandwidth of greater than 12.5 MHz.

The method 170 further includes processing the communicated data at 188. For example, the data may be digitized and/or processed to generate one or more images, such as ultrasound images.

Thus, various embodiments may provide an ultrasound system that is capable of operating at an increased effective bandwidth without system reconfiguration or redesign.

It should be noted that the various embodiments may be implemented in different ultrasound systems and/or in different portions or components of the ultrasound system. For example, various embodiments may be implemented in connection with an ultrasound system wherein a front end is connected to a back end via a plurality of data channels that communicate ultrasound element data from the front end to the back end. It should be noted that the ultrasound system may be as system capable of electrical or mechanical steering of a sound beam (such as in 3D space) and is configurable to acquire information corresponding to a plurality of 2D representations or images (or optionally 3D and 4D images) of a region of interest (ROI) in a subject or patient, which may be defined or adjusted as described in more detail herein. The ultrasound system is configurable to acquire 2D images, for example, in one or more planes of orientation.

It should be noted that although the various embodiments may be described in connection with an ultrasound system, the methods and systems are not limited to ultrasound imaging or a particular configuration thereof. The various embodiments may be implemented in connection with different types of imaging systems, including, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

Figure 5:
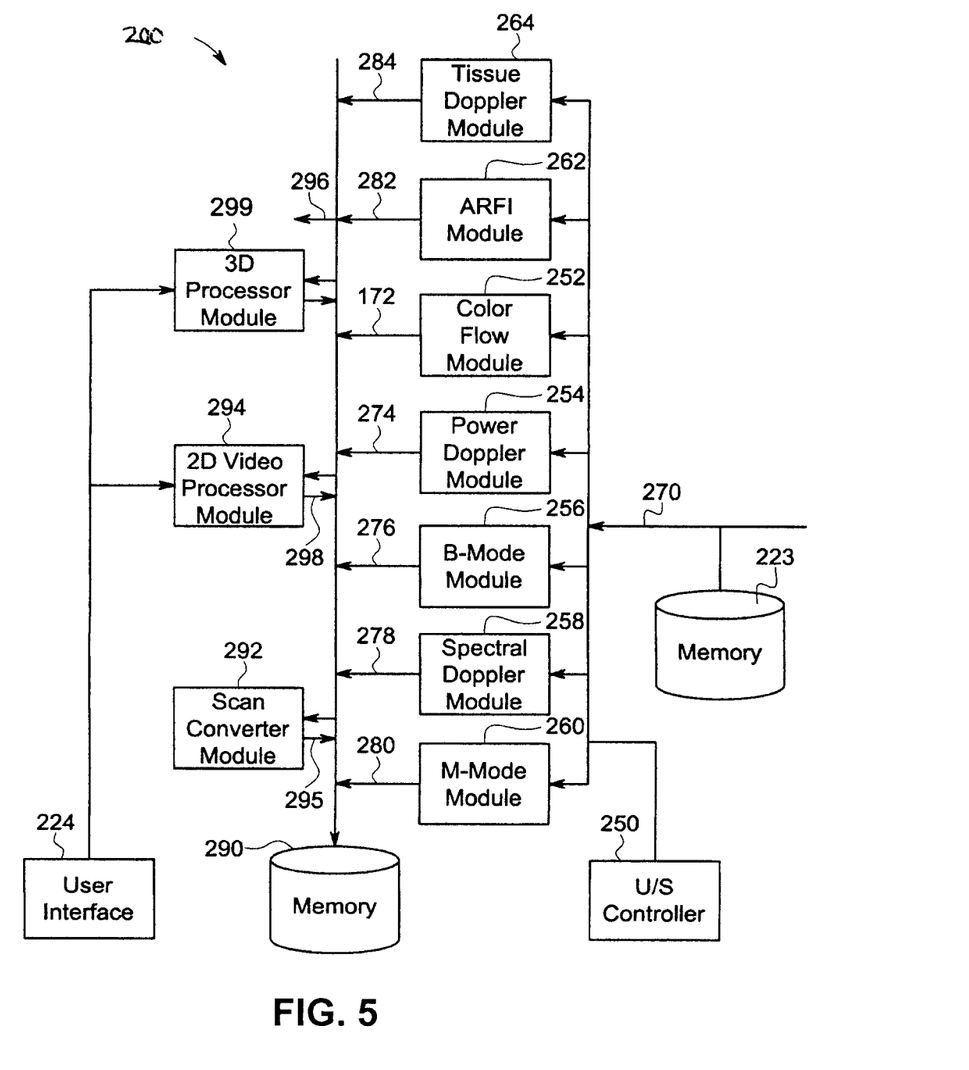
FIG. 5 is a block diagram of an ultrasound processor formed in accordance with various embodiments.

FIG. 5 illustrates an exemplary block diagram of an ultrasound processor module 200, which may be embodied as the processor 136 of FIG. 2 or a portion thereof. The ultrasound processor module 200 is illustrated conceptually as a collection of sub-modules or circuits, but may be implemented utilizing any combination of dedicated hardware boards, DSPs, processors, etc. Alternatively, the sub-modules of FIG. 5 may be implemented utilizing an off-the-shelf PC with a single processor or multiple processors, with the functional operations distributed between the processors, for example also including a Graphics Processor Unit (GPU). As a further option, the sub-modules of FIG. 5 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules or sub-components illustrated in FIG. 5 may be controlled by a local ultrasound controller 250 or by the processor module 200. The sub-modules 252-264 perform mid-processor operations. The ultrasound processor module 236 may receive ultrasound data 270 in one of several forms. In the embodiment of FIG. 5, the received ultrasound data 270 constitutes I,Q data pairs representing the real and imaginary components associated with each data sample. The I,Q data pairs are provided to one or more of a color-flow sub-module 252, a power Doppler sub-module 254, a B-mode sub-module 256, a spectral Doppler sub-module 258 and an M-mode sub-module 260. Optionally, other sub-modules may be included such as an Acoustic Radiation Force Impulse (ARFI) sub-module 262 and a Tissue Doppler (TDE) sub-module 264, among others.

Each of sub-modules 252-264 are configured to process the I,Q data pairs in a corresponding manner to generate color-flow data 272, power Doppler data 274, B-mode data 276, spectral Doppler data 278, M-mode data 280, ARFI data 282, and tissue Doppler data 284, all of which may be stored in a memory 290 (or memory 214 or memory 222 shown in FIG. 5) temporarily before subsequent processing. For example, the B-mode sub-module 256 may generate B-mode data 276 including a plurality of B-mode image planes, such as in a biplane or triplane image acquisition as described in more detail herein.

The data 272-284 may be stored in the memory 290, for example, as sets of vector data values, where each set defines an individual ultrasound image frame. The vector data values are generally organized based on the polar coordinate system. Alternately or additionally, the data may be stored as beamformed I,Q data in the memory 223. In some embodiments, channel I,Q data before beamforming may be stored.

A scan converter sub-module 292 accesses and obtains from the memory 290 the vector data values associated with an image frame and converts the set of vector data values to Cartesian coordinates to generate an ultrasound image frame 294 formatted for display. The ultrasound image frames 295 generated by the scan converter module 292 may be provided back to the memory 290 for subsequent processing or may be provided to the memory 214 or the memory 222.

Once the scan converter sub-module 292 generates the ultrasound image frames 295 associated with, for example, B-mode image data, and the like, the image frames may be restored in the memory 290 or communicated over a bus 296 to a database (not shown), the memory 214, the memory 222 and/or to other processors.

The scan converted data may be converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 138 (shown in FIG. 62, which may include one or more monitors or windows of the display, to display the image frame. The image displayed in the display 138 is produced from image frames of data in which each datum indicates the intensity or brightness of a respective pixel in the display.

Referring again to FIG. 5, a 2D video processor sub-module 294 combines one or more of the frames generated from the different types of ultrasound information. For example, the 2D video processor sub-module 294 may combine a different image frames by mapping one type of data to a grey map and mapping the other type of data to a color map for video display. In the final displayed image, color pixel data may be superimposed on the grey scale pixel data to form a single multi-mode image frame 298 (e.g., functional image) that is again re-stored in the memory 290 or communicated over the bus 296. Successive frames of images may be stored as a cine loop in the memory 290 or memory 140 (shown in FIG. 2). The cine loop represents a first in, first out circular image buffer to capture image data that is displayed to the user. The user may freeze the cine loop by entering a freeze command at the user interface 224. The user interface 224 may include, for example, a keyboard and mouse and all other input controls associated with inputting information into the ultrasound system 100 (shown in FIG. 2).

A 3D processor sub-module 299 is also controlled by the user interface 124 and accesses the memory 290 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

Figure 6:
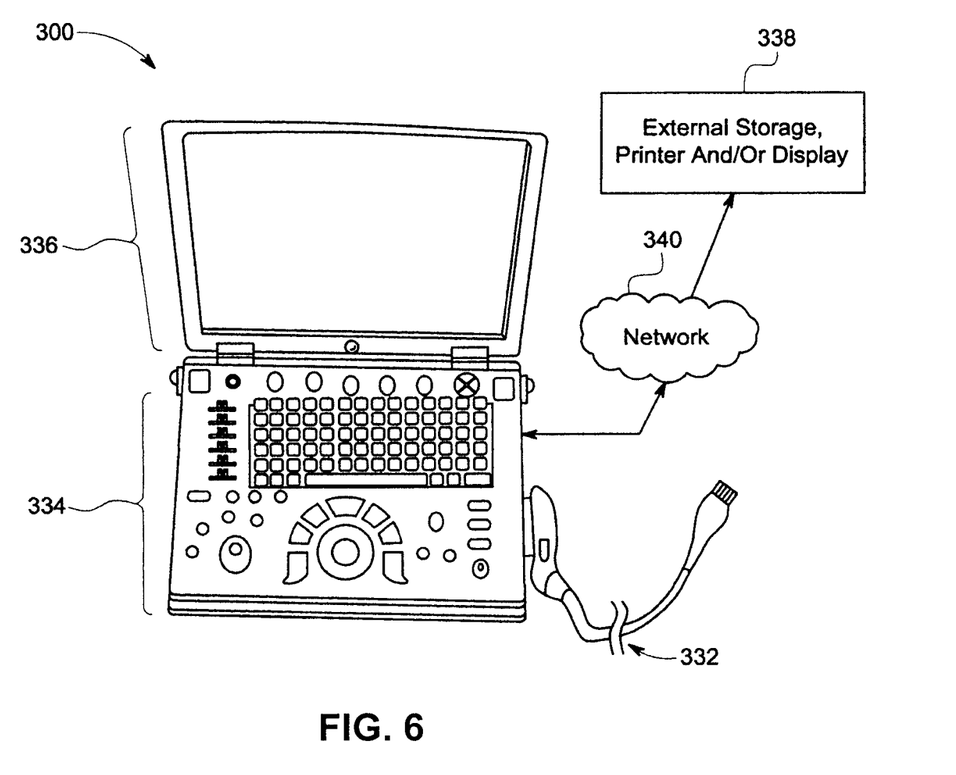
FIG. 6 is a diagram illustrating a miniaturized ultrasound system in which various embodiments may be implemented.
Figure 7:
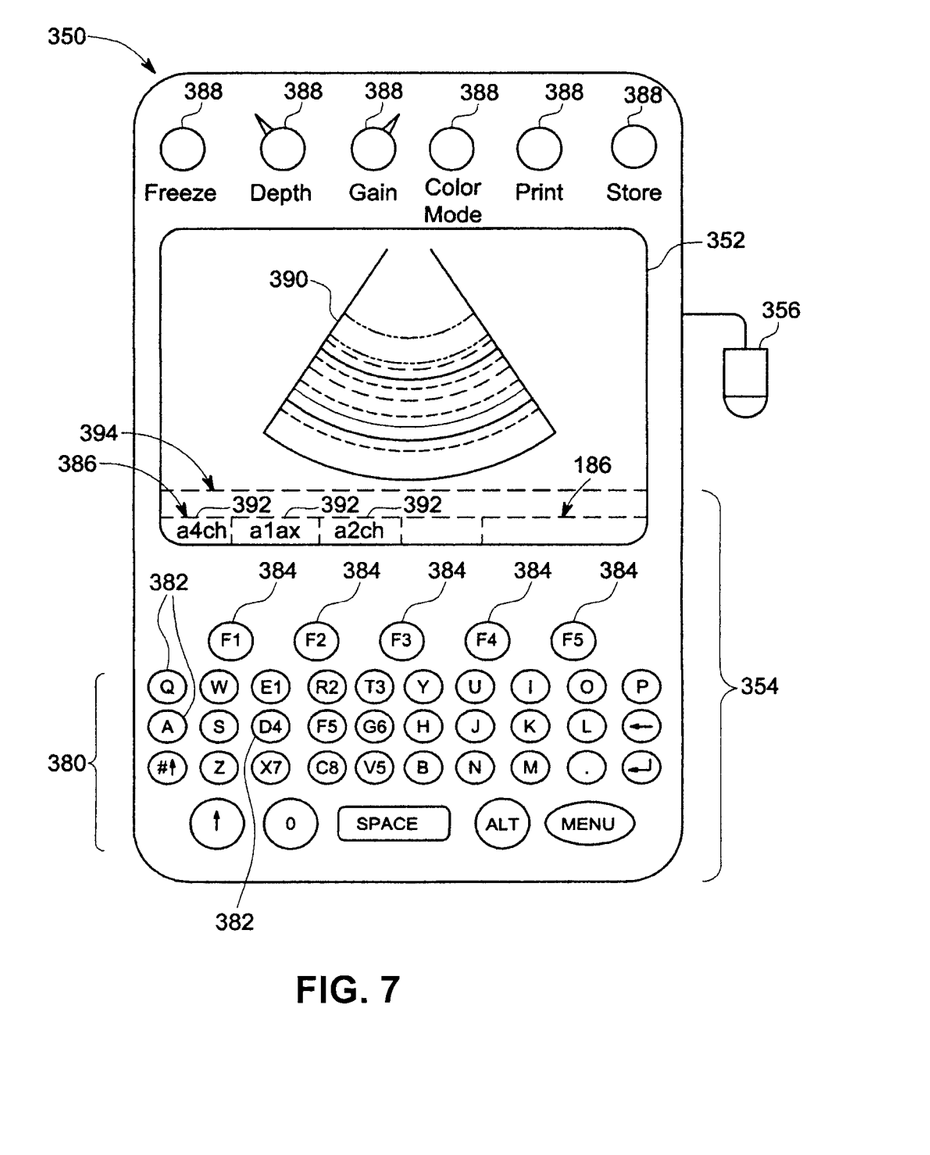
FIG. 7 is a diagram illustrating a hand carried or pocket-sized ultrasound imaging system in which various embodiments may be implemented.
Figure 8:
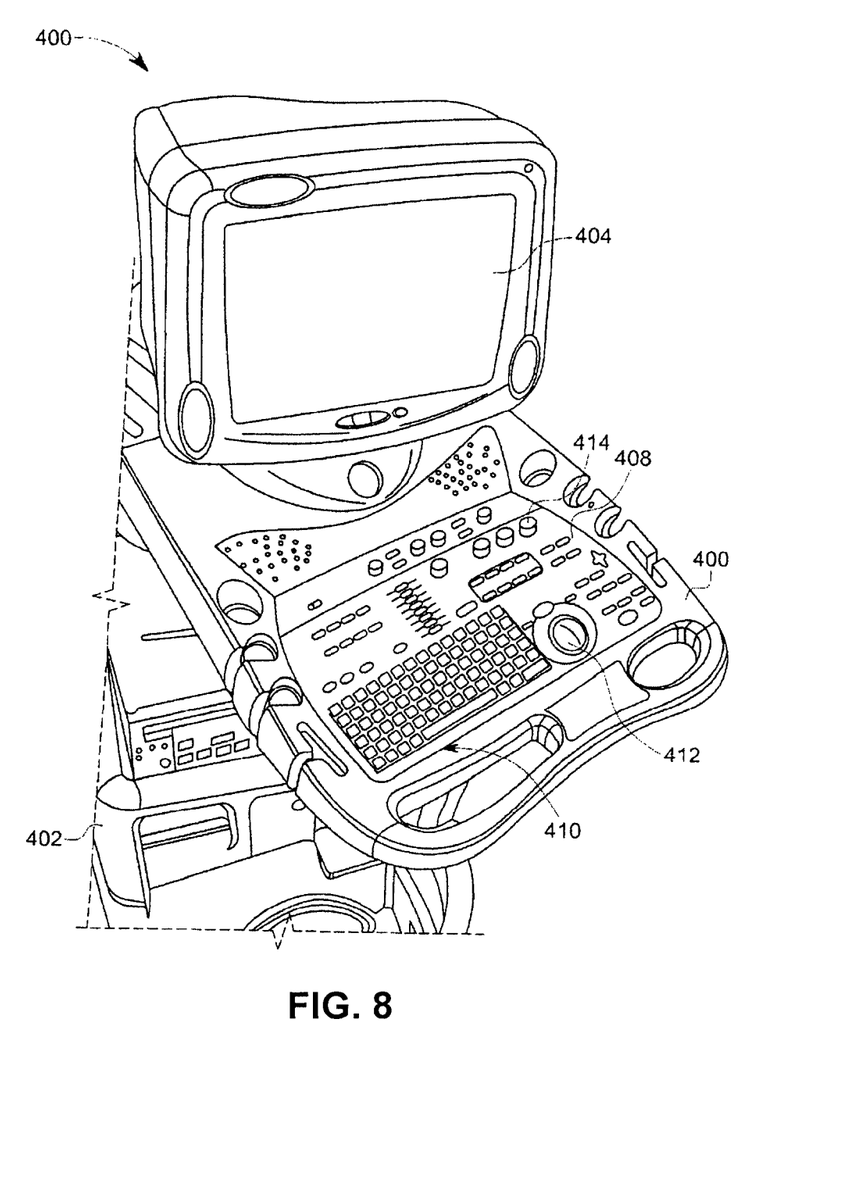
FIG. 8 is a diagram illustrating a console type ultrasound imaging system in which various embodiments may be implemented.

The ultrasound system 100 of FIG. 2 may be embodied in a small-sized system, such as laptop computer or pocket sized system as well as in a larger console-type system. FIGS. 6 and 7 illustrate small-sized systems, while FIG. 8 illustrates a larger system.

FIG. 6 illustrates a 3D-capable miniaturized ultrasound system 300 having a probe 332 that may be configured to acquire 3D ultrasonic data or multi-plane ultrasonic data. For example, the probe 332 may have a 2D array of elements 124 as discussed previously with respect to the probe 126 of FIG. 2. A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 330 and of displaying or printing images that may have greater resolution than the integrated display 336.

FIG. 7 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, an ultrasound probe 356. The display 352 may be, for example, a 320×320 pixel color LCD display (on which a medical image 390 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 300 may provide the same scanning and processing functionality as the system 100 (shown in FIG. 2).

FIG. 8 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412, and/or multi-function controls 414 may be provided.

It should be noted that the various embodiments may be implemented in hardware, software or a combination thereof. The various embodiments and/or components, for example, the circuits, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "circuit" may include any processor-based or microprocessor-based system including systems using microcontrollers, reduced instruction set computers (RISC), SISCs (e.g., ARM processors), ASICs, logic circuits, and any other circuit or processor capable of executing the functions described herein. The above examples are exemplary only, and are thus not intended to limit in any way the definition and/or meaning of the term "computer."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or circuits, a program circuit within a larger program or a portion of a program circuit. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for communicating data in an ultrasound system, the method comprising:

acquiring ultrasound data using an ultrasound probe having a plurality of transducer elements, the ultrasound data including echo information acquired from the plurality of transducer elements, the ultrasound data including at least first and second data subsets acquired using a plurality of transmit events of the ultrasound probe, the second data subset acquired with a time shift relative to the first data subset where the time shift is a portion of a sampling time period;

digitizing the ultrasound data that is acquired; and combining the at least first and second subsets of the acquired ultrasound data by interleaving the first data subset and the second data subset and communicating the acquired ultrasound data that is combined for at least some of the plurality of transmit events to a receive beamformer, the first and second subsets of communicated digitized ultrasound data being different for the plurality of transmit events.

2. The method of claim 1, wherein the acquired ultrasound data from each of the at least first and second data subsets is communicated at half of a sampling rate of an analog to digital converter (ADC) of the ultrasound probe.

3. The method of claim 1, wherein the combining comprises combining the first subset of the ultrasound data that is acquired from one-half of a plurality of system channels in one of the plurality of transmit events with the one-half of the plurality of system channels in another one of the plurality of transmit events.

4. The method of claim 1, wherein the combining comprises combining the first subset of the ultrasound data that is acquired from one-half of the ultrasound data in one of the plurality of transmit events with the one-half of the ultrasound data in another one of the plurality of transmit events.

5. The method of claim 4, further comprising demodulating a one-half band of the ultrasound data in one of the plurality of transmit events and demodulating the other one-half band of the ultrasound data in the other one of the plurality of transmit events.

6. The method of claim 1, wherein the combining comprises combining the first subset of the ultrasound data that is acquired by demodulating and communicating an in-phase component (I) of the acquired ultrasound data on one of the plurality of transmit events and demodulating and communicating a quadrature component (Q) on another one of the plurality of transmit events.

7. The method of claim 1, wherein the acquiring includes receiving the echo information from plural sequentially transmitted ultrasound waves and the combining is performed on the ultrasound data acquired from the sequentially transmitted ultrasound waves.

8. The method of claim 1, wherein the acquiring includes receiving the echo information from plural, non-sequentially transmitted ultrasound waves and the combining is performed on the ultrasound data acquired from the non-sequentially transmitted ultrasound waves.

9. The method of claim 1, wherein the plurality of transmit events are defined by a same ultrasound firing of the plurality of transducer elements.

10. An ultrasound system comprising:

an ultrasound probe having a transducer array for acquiring ultrasound data including echo information during an imaging mode of operation, the ultrasound probe configured to acquire the ultrasound data including at least first and second data subsets acquired using a plurality of transmit events, the second data subset acquired with a time shift relative to the first data set, wherein the time shift is a portion of a sampling time period;

a digitizer configured to digitize the ultrasound data that is acquired; and a transmit event controller configured to combine at least first and second subsets of the acquired ultrasound data from the plurality of transmit events by interleaving the subsets of the acquired ultrasound data from the plurality of transmit events, the transmit event controller also configured to communicate the at least first and second subsets of the acquired ultrasound data for at least some of the plurality of transmit events to a receive beamformer, wherein the first and second subsets of communicated digitized ultrasound data are different for the plurality transmit events.

11. The ultrasound system of claim 10, wherein the acquired ultrasound data from each of the first and second subsets is communicated at half of a sampling rate of an analog to digital converter (ADC) of the ultrasound probe.

12. The ultrasound system of claim 10, wherein the transmit event controller is configured to control the combining of the first and second subsets of the acquired ultrasound data by combining a subset of the acquired ultrasound data from one-half of a plurality of system channels in one of the plurality of transmit events with the one-half of the plurality of system channels in another one of the plurality of transmit events.

13. The ultrasound system of claim 10, wherein the transmit event controller is configured to control the combining of the first and second subsets of the acquired ultrasound data by combining the first subset of the acquired ultrasound data from one-half of the ultrasound data in one of the plurality of transmit events with the one-half of the ultrasound data in another one of the plurality of transmit events.

14. The ultrasound system of claim 10, wherein the transmit event controller is configured to control the combining of the first and second subsets of the acquired ultrasound data by combining the first subset of the acquired ultrasound data by demodulating and communicating an in-phase component (I) of the acquired ultrasound data on one of the plurality of transmit events and demodulating and communicating a quadrature component (Q) on another one of the plurality of transmit events.

15. The ultrasound system of claim 10, wherein the transmit event controller is configured to control the combining of the first and second subsets of the acquired ultrasound data by combining the first and second subsets of the acquired ultrasound data from one of sequential transmit events or non-sequential transmit events.

16. The ultrasound system of claim 10, wherein the transmit event controller is configured to control the combining of the first and second subsets of the acquired ultrasound data by combining the first and second subsets of the acquired ultrasound data from the plurality of transmit events that are defined by a same ultrasound firing of a plurality of transducer elements of the transducer array.

* * * * *